(12) United States Patent
Kurihara et al.

(10) Patent No.: US 9,765,412 B2
(45) Date of Patent: Sep. 19, 2017

(54) PROCESS OF PRODUCING SUGAR SOLUTION

(71) Applicant: Toray Industries, Inc., Tokyo (JP)

(72) Inventors: Hiroyuki Kurihara, Kamakura (JP); Katsushige Yamada, Kamakura (JP)

(73) Assignee: Toray Industries, Inc. (JP)

( * ) Notice: Subject to any disclaimer, the term of this patent is extended or adjusted under 35 U.S.C. 154(b) by 0 days.

(21) Appl. No.: 14/405,239

(22) PCT Filed: Jun. 4, 2013

(86) PCT No.: PCT/JP2013/065431
§ 371 (c)(1),
(2) Date: Dec. 3, 2014

(87) PCT Pub. No.: WO2013/183617
PCT Pub. Date: Dec. 12, 2013

(65) Prior Publication Data
US 2015/0147787 A1    May 28, 2015

(30) Foreign Application Priority Data

Jun. 5, 2012 (JP) ................................ 2012-127704

(51) Int. Cl.
*C13K 1/04* (2006.01)
*C12P 19/02* (2006.01)
(Continued)

(52) U.S. Cl.
CPC ................. *C13K 1/04* (2013.01); *C12P 7/56* (2013.01); *C12P 19/02* (2013.01); *C12P 19/14* (2013.01); *C13K 13/002* (2013.01); *C12P 2203/00* (2013.01)

(58) Field of Classification Search
CPC ...................................................... C13K 1/04
See application file for complete search history.

(56) References Cited

U.S. PATENT DOCUMENTS 2,073,616 A * 3/1937 Acree ................. C08B 37/0036
106/164.01
2,892,683 A * 6/1959 Giacinto ................... C01F 5/22
210/733

(Continued)

FOREIGN PATENT DOCUMENTS

CN          101348429        1/2009
JP          7-67399 B2       7/1995
(Continued)

OTHER PUBLICATIONS

MSDS for tetrasodium pyrophosphate Innophos bulletin, pp. 1-11, Sep. 4, 2007.*

(Continued)

*Primary Examiner* — Douglas B Call
(74) *Attorney, Agent, or Firm* — DLA Piper LLP (US)

(57) ABSTRACT

A method produces a sugar liquid from a cellulosic biomass material, which sugar liquid has improved fermentability. The method produces a sugar liquid by: adding an alkali(s) to a concentrated cellulosic biomass sugar liquid to adjust the pH to not less than 7 to precipitate an insoluble substance (s) containing at least magnesium; and performing filtration through a microfiltration membrane to remove the insoluble substance(s), to obtain a sugar liquid as a permeate.

13 Claims, 5 Drawing Sheets

(51) Int. Cl.
   *C12P 19/14*    (2006.01)
   *C12P 7/56*     (2006.01)
   *C13K 13/00*    (2006.01)

(56) References Cited

U.S. PATENT DOCUMENTS

| | | | | |
|---|---|---|---|---|
| 3,972,775 | A * | 8/1976 | Wilke | C12P 19/14 435/163 |
| 4,743,682 | A * | 5/1988 | Lee | A23J 3/34 210/687 |
| 4,925,690 | A * | 5/1990 | Odake | A23L 2/74 426/330.5 |
| 5,782,982 | A * | 7/1998 | Farone | C08B 15/02 127/1 |
| 2009/0061490 | A1 * | 3/2009 | Edwards | C12P 1/02 435/105 |
| 2010/0184151 | A1 * | 7/2010 | Tolan | C12P 7/10 435/72 |
| 2013/0092157 | A1 * | 4/2013 | Hanakawa | C13B 20/165 127/53 |

FOREIGN PATENT DOCUMENTS

| | | |
|---|---|---|
| JP | 7-242788 A | 9/1995 |
| JP | 2001-157599 A | 6/2001 |
| JP | 2005-278407 | 10/2005 |
| JP | 2006-304634 A | 11/2006 |
| WO | 2009/041009 A1 | 4/2009 |
| WO | WO 2011/162009 * | 4/2011 |
| WO | 2011/162009 A1 | 12/2011 |

OTHER PUBLICATIONS

Supplementary European Search Report dated Nov. 9, 2015 of corresponding European Application No. 13801065.7.

* cited by examiner

PROCESS OF PRODUCING SUGAR SOLUTION

TECHNICAL FIELD

This disclosure relates to a method of producing a sugar liquid from biomass.

BACKGROUND

In recent years, methods of producing a sugar liquid by pretreating cellulosic biomass with an acid, hot water, alkali or the like and then adding cellulase thereto to perform hydrolysis have been widely studied. The thus obtained sugar liquid sometimes has a lower sugar concentration than a conventional sugar liquid derived from an edible material such as starch or cane juice.

In general, when the sugar concentration is low, the sugar concentration can be increased by distilling water in the sugar liquid by, for example, concentration under reduced pressure or concentration by heating. For example, when beet molasses is concentrated in an evaporator has been disclosed (see JP 2005-278407 A).

On the other hand, in methane fermentation treatment of organic wastes, there have been troubles caused by precipitation of alkaline earth metals including calcium and magnesium contained in the wastes such as clogging of pipes and deterioration of functions of separation membranes due to their attachment on the membrane surfaces (see WO 2009/041009).

We found problems in culture of microorganisms using as a fermentation feedstock a cellulosic biomass sugar liquid, especially concentrated cellulosic biomass sugar liquid, that precipitation of an insoluble substance containing magnesium as a major component may cause attachment of scale to a fermentation apparatus, clogging of pipes, clogging of a separation membrane, occurrence of a trouble in a pH/DO sensor, attachment of scale to a separation membrane during continuous culture, and difficulty in membrane separation of a fermentation product from the culture liquid.

It could therefore be helpful to provide a method of producing a sugar liquid, which method can prevent the above problems, that is, attachment of scale to a fermentation apparatus, clogging of pipes, clogging of a separation membrane, occurrence of a trouble in a pH/DO sensor and attachment of scale to a separation membrane during continuous culture, and enables membrane separation of a fermentation product from the culture liquid.

SUMMARY

We thus provide a method of producing a sugar liquid comprising adding an alkali(s) to a concentrated cellulosic biomass sugar liquid to adjust the pH to not less than 7 to precipitate an insoluble substance(s) containing at least magnesium; and performing filtration through a microfiltration membrane to remove the insoluble substance(s) to obtain a sugar liquid as a permeate.

Preferably, the concentrated cellulosic biomass sugar liquid is a sugar liquid prepared by subjecting a hydrolysate obtained from a cellulosic biomass by any one or more of treatments selected from the group consisting of hydrothermal treatment, acid treatment, alkali treatment and enzyme treatment, to any one or more of treatments selected from the group consisting of membrane concentration, concentration under reduced pressure and concentration by heating.

Preferably, the pH of the concentrated cellulosic biomass sugar liquid is adjusted to not less than 8 with the alkali(s).

Preferably, the average pore size of the microfiltration membrane is 0.01 μm to 1 μm.

Preferably, the microfiltration membrane is a hollow fiber microfiltration membrane.

Preferably, one or more additives selected from the group consisting of nitrogen sources, metal salts, vitamins, amino acids, sugars, antifoaming agents and surfactants are further added.

Various kinds of chemical products can be produced using the sugar liquid obtained by the production method as a fermentation feedstock.

A microorganism is cultured using, as a fermentation feedstock, a sugar liquid obtained by the above production method to allow production of a chemical product in the culture liquid, while the microorganism and the chemical product are continuously or intermittently filtered through a separation membrane. By this, the chemical product can be recovered.

The above-mentioned problem, that is, attachment of scale to a fermenter or a separation membrane can be suppressed without using an expensive method such as ion chromatography. This can be achieved by a simple method in which the following operations are carried out: an alkali(s) is/are added to a concentrated cellulosic biomass sugar liquid to adjust the pH to not less than 7 to precipitate an insoluble substance(s) containing at least magnesium; and the insoluble substance(s) is/are then removed by filtration through a microfiltration membrane, to obtain a sugar liquid as a permeate. In addition, improvement of the fermentation yield can be achieved by performing the above operations when a concentrated cellulosic biomass sugar liquid is used as a fermentation feedstock.

The method of producing a sugar liquid can be used to produce a sugar liquid to be used as a fermentation feedstock from a cellulose-containing biomass. The sugar liquid produced by our methods can be used as a fermentation feedstock for various kinds of chemical products.

DESCRIPTION OF SYMBOLS

Figure 1:
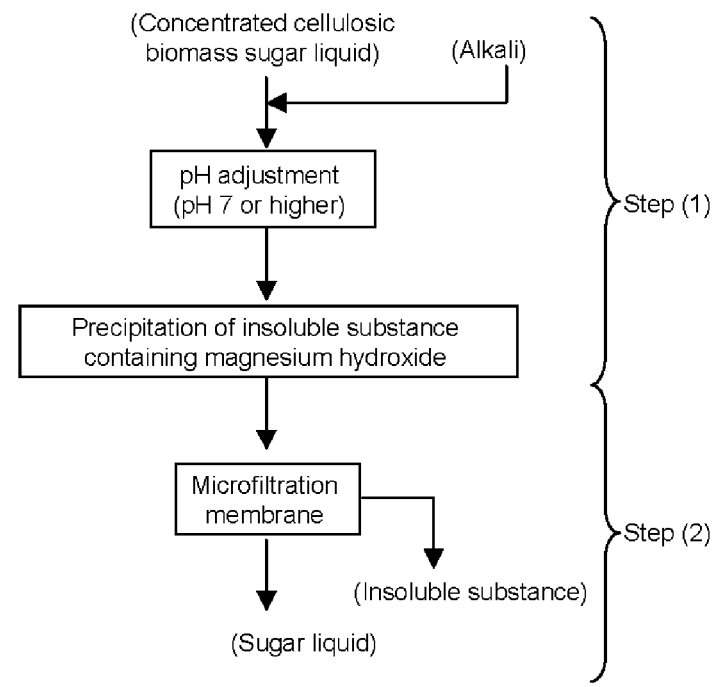
FIG. 1 is a diagram illustrating the block flow of a method of producing a sugar liquid.

1. Precipitation tank
2. Thermostat
3. Diffuser tube
4. pH sensor

5. Alkali supply pump
6. Alkali storage tank
7. Microfiltration membrane pump
8. Microfiltration membrane module
9. Compressed air supplier
10. Reverse washing pump
11. MF filtrate tank
12. Acid supply line
13. Washing valve
14. Cross-flow return line
15. Fermentation apparatus
16. Vent pipe
17. DO sensor
18. Incubator
19. Stirrer
20. pH sensor (fermentation)
21. Fermenter
22. Acid supply tank
23. Alkali supply tank
24. Microfiltration membrane module
25. Cross-flow pump
26. Culture filtrate storage tank
27. Sugar liquid flow rate controller
28. Silicone tube
29. Silicone adhesive
30. Hollow fiber microfiltration membrane

DETAILED DESCRIPTION

The method of producing a sugar liquid comprises the steps of: adding an alkali(s) to a concentrated cellulosic biomass sugar liquid to adjust the pH to not less than 7 to precipitate an insoluble substance(s) containing at least magnesium; and performing filtration through a microfiltration membrane to remove the insoluble substance(s), to obtain a sugar liquid as a permeate.

FIG. 1 is a diagram illustrating the block flow of a method of producing a sugar liquid.

First, the step of adding an alkali(s) to a concentrated cellulosic biomass sugar liquid to adjust the pH to not less than 7 to precipitate an insoluble substance(s) containing at least magnesium [Step (1)] is described.

The concentrated cellulosic biomass sugar liquid to be used means a sugar liquid which is an aqueous solution containing a sugar obtained by hydrolysis of a cellulosic biomass material and has been processed through a step of concentration by one or more concentration operations. The cellulosic biomass herein means a biomass containing cellulose.

Specific examples of the cellulosic biomass include herbaceous biomasses such as bagasse, switchgrass, napier grass, *Erianthus*, corn stover, rice straw, wheat straw, chaff and coconut husk; woody biomasses such as trees, poplar and waste building materials; and water environment-derived biomasses such as algae and seaweeds.

Such biomasses contain, in addition to cellulose and hemicellulose (which may be hereinafter referred to as "cellulose" as a general term for cellulose and hemicellulose), lignin as aromatic macromolecules and the like.

The sugar liquid herein means a sugar liquid obtained by subjecting the cellulosic biomass to one or more treatments selected from the group consisting of acid treatment, enzyme treatment, alkali treatment and pulverization treatment to perform hydrolysis of the cellulose component and/or hemicellulose component contained in the cellulosic biomass. The sugar liquid is not limited to the sugar liquid immediately after the hydrolysis, and an aqueous solution obtained after adding a microorganism to the hydrolysate and performing fermentation can also be regarded as the sugar liquid as long as the aqueous solution contains a sugar, and can be used.

Major sugar components of the hydrolysate are hexoses such as glucose, and pentoses such as xylose. The concentrated sugar liquid means a sugar liquid prepared by concentrating the cellulosic biomass sugar liquid by a known method such as evaporative concentration or membrane concentration. The concentration method may be a combination of a plurality of methods. The concentrated sugar liquid may also be a dilution prepared by adding water or the like to a liquid concentrated by the above concentration method, or to a sugar in the solid state prepared by removal of water by concentration.

The operation of adding an alkali(s) to a concentrated cellulosic biomass sugar liquid to adjust the pH to not less than 7 to precipitate an insoluble substance(s) containing at least magnesium, is carried out.

Preferred examples of the alkali(s) to be added include ammonia, aqueous ammonia, sodium hydroxide and potassium hydroxide.

Although an alkali such as calcium hydroxide may also be used, calcium may cause production of scale similarly to magnesium so that use of such an alkali is not advantageous. As the alkali, ammonia is especially preferably used.

When sulfuric acid is used in the hydrolysis of cellulosic biomass, the obtained hydrolysate, as well as the concentrated sugar liquid, often contain sulfate ions. By adding ammonia thereto, ammonium sulfate can be produced as a salt. As is well known, ammonium sulfate can be effectively used as a nitrogen source by microorganisms during their growth, fermentation production and the like. That is, the alkali to be used for the pH adjustment is most preferably ammonia. By adjusting the pH to not less than 7, magnesium dissolved in the concentrated cellulosic biomass sugar liquid can be made into magnesium hydroxide, which can be precipitated as insoluble crystals. The pH is adjusted to preferably not less than 8, more preferably not less than 9, most preferably not less than 10. The upper limit of the pH is not limited as long as the pH is less than 14, but, since a pH higher than 12 does not especially increase the effect, the pH is preferably not more than 12 in view of reducing the amount of the alkali(s) used. That is, the pH is preferably 8 to 12, more preferably 9 to 12, most preferably 10 to 12.

Examples of the method of feeding the alkali(s) to adjust the pH include a method in which the concentrated cellulosic biomass sugar liquid is preliminarily subjected to titration with the alkali(s) to be used, and a predetermined amount(s) of the alkali(s) is/are fed; and a method in which the alkali(s) is/are fed while the increase in the pH is monitored with a pH sensor or the like until a predetermined pH is achieved.

For homogenization of the alkali(s) added, an operation such as stirring or mixing may be carried out. After the adjustment to the alkaline pH, precipitation of magnesium hydroxide may be carried out, if necessary, by an operation such as incubation or cooling. The time of the precipitation may be arbitrary set, and the precipitation is carried out for preferably not less than 1 minute, more preferably not less than 5 minutes, most preferably not less than 3 hours.

The longer the time of the precipitation after the adjustment to the alkaline pH, the higher the effect to sufficiently precipitate magnesium hydroxide. This treatment also has an effect of disinfection, elimination and/or sterilization by exposure of microorganisms, molds, spores and/or the like contained in the sugar liquid to alkaline conditions.

Figure 2:
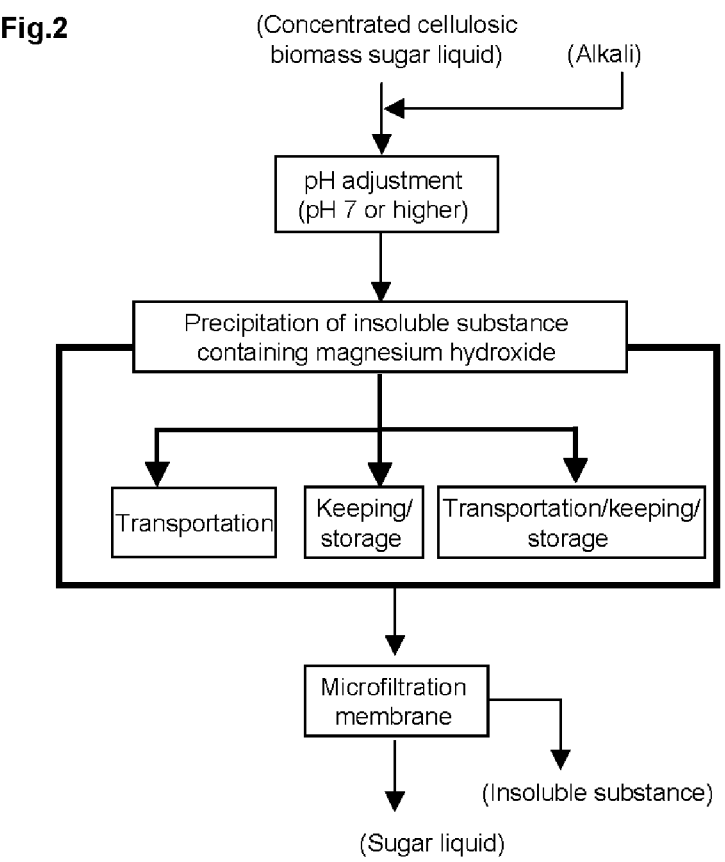
FIG. 2 is a diagram illustrating the block flow of another method of producing a sugar liquid.

FIG. 2 is a diagram illustrating the block flow of another method of producing a sugar liquid. In FIG. 2, the diagram shows a flow that utilizes, in the step of precipitation of magnesium hydroxide, a period such as transportation, keeping/storage, or transportation/keeping/storage of the concentrated cellulosic biomass sugar liquid. Since the precipitation of the insoluble substance(s) requires a certain period of time, the above periods can be effectively utilized for the purpose. Since the pH is adjusted with an alkali(s) as described above, an improved keeping quality due to prevention of microbial contamination and the like can be achieved.

The microfiltration membrane treatment may be preceded by addition of one or more of nutrients and auxiliary materials required for use of a sugar liquid as a fermentation feedstock such as nitrogen sources, metal salts, vitamins, amino acids, sugars, antibiotics, surfactants and anti-foaming agents.

Examples of the nitrogen sources include ammonium sulfate, ammonium phosphate, casein, meat extract, yeast extract, peptone, soy peptone and corn steep liquor.

Examples of the metal salts include those of molybdenum, cobalt, iron, copper, zinc, manganese, nickel, chrome, selenium, iodine, fluorine, silicon and vanadium. Examples of the vitamins include vitamin B12, thiamine, biotin and vitamin B1.

Examples of the sugars include glucose, arabinose, xylose, fructose, psicose, galactose, mannose, xylulose, threose, erythrose and ribose. Examples of the amino acids include alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine and valine.

Examples of the antibiotics include tetracycline antibiotics, β-lactam antibiotics, aminoglycoside antibiotics, macrolide antibiotics and chloramphenicol antibiotics.

Examples of the surfactants include nonionic surfactants, anionic surfactants and cationic surfactants.

In terms of addition of such components in cases of using a sugar liquid as the fermentation feedstock, necessary components in required amounts are preferably preliminarily added at this stage. This is carried out for the purpose of preventing the insoluble substance(s) from being generated again during the stage of fermentation due to addition of these components to the sugar liquid.

The concentrated cellulosic biomass sugar liquid is preferably a sugar liquid prepared by concentration using a nanofiltration membrane and/or reverse osmosis membrane. The nanofiltration membrane is also called a nanofilter (nanofiltration membrane, NF membrane), and generally defined as a "membrane that allows permeation of monovalent ions, but blocks divalent ions." The membrane is considered to have fine voids having sizes of about several nanometers, and mainly used to block fine particles, molecules, ions, salts and the like in water.

A reverse osmosis membrane is also called an RO membrane, and generally defined as a "membrane having a desalting function also for monovalent ions." The membrane is considered to have ultrafine voids having sizes of about several angstroms to several nanometers, and mainly used for removal of ion components such as seawater desalination and ultrapure water production.

The material of the nanofiltration membrane or reverse osmosis membrane may be composed of a macromolecular compound, and examples of the macromolecular compound include cellulose acetate polymers, polyamides, polyesters, polyimides, vinyl polymers and polysulfones. The membrane is not limited to a membrane constituted by one of the materials, and may be a membrane comprising a plurality of the membrane materials.

As the nanofiltration membrane, a spiral-wound membrane element is preferred. Specific examples of preferred nanofiltration membrane elements include a cellulose acetate nanofiltration membrane element GE Sepa, manufactured by GE Osmonics; nanofiltration membrane elements NF99 and NF99HF, manufactured by Alfa-Laval, which have polyamide functional layers; nanofiltration membrane elements NF-45, NF-90, NF-200, NF-270 and NF400, manufactured by FilmTec Corporation, which have cross-linked piperazine polyamide functional layers; and nanofiltration membrane elements SU-210, SU-220, SU-600 and SU-610, manufactured by Toray Industries, Inc., comprising a nanofiltration membrane UTC60, manufactured by the same manufacturer, which comprises a cross-linked piperazine polyamide as a major component. The nanofiltration membrane element is more preferably NF99, NF99HF; NF-45, NF-90, NF-200, NF-400, SU-210, SU-220, SU-600 or SU-610. The nanofiltration membrane element is still more preferably SU-210, SU-220, SU-600 or SU-610.

Examples of the reverse osmosis membrane include composite membranes comprising a cellulose acetate polymer as a functional layer (hereinafter also referred to as cellulose acetate reverse osmosis membranes) and composite membranes comprising a polyamide as a functional layer (hereinafter also referred to as polyamide reverse osmosis membranes).

Examples of the cellulose acetate polymer herein include polymers prepared with one of, or a mixture or mixed ester of two or more of, organic acid esters of cellulose such as cellulose acetate, cellulose diacetate, cellulose triacetate, cellulose propionate and cellulose butyrate. Examples of the polyamide include linear polymers and cross-linked polymers composed of aliphatic and/or aromatic diamine monomers.

Specific examples of the reverse osmosis membrane include polyamide reverse osmosis membrane modules manufactured by TORAY INDUSTRIES, INC. SUL-G10 and SUL-G20, which are ultralow-pressure type modules, and SU-710, SU-720, SU-720F, SU-710L, SU-720L, SU-720LF, SU-720R, SU-710P and SU-720P, which are low-pressure type modules, as well as SU-810, SU-820, SU-820L and SU-820FA, which are high-pressure type modules containing UTC80 as a reverse osmosis membrane; cellulose acetate reverse osmosis membranes manufactured by the same manufacturer SC-L100R, SC-L200R, SC-1100, SC-1200, SC-2100, SC-2200, SC-3100, SC-3200, SC-8100 and SC-8200; NTR-759HR, NTR-729HF, NTR-70SWC, ES10-D, ES20-D, ES20-U, ES15-D, ES15-U and LF10-D, manufactured by Nitto Denko Corporation; RO98pHt, RO99, HR98PP and CE4040C-30D, manufactured by Alfa-Laval; GE Sepa, manufactured by GE; BW30-4040, TW30-4040, XLE-4040, LP-4040, LE-4040, SW30-4040 and SW30HRLE-4040, manufactured by FilmTec Corporation; TFC-HR and TFC-ULP, manufactured by KOCH; and ACM-1, ACM-2 and ACM-4, manufactured by TRISEP.

The use of the nanofiltration membrane and/or reverse osmosis membrane to concentrate the sugar liquid has an advantage that the sugar concentration in the sugar liquid can be increased and fermentation inhibitors can be removed as a permeate. The term "fermentation inhibitors" herein means components, other than sugars, that inhibit fermentation in the fermentation step at a later stage, and specific examples of the fermentation inhibitors include aromatic compounds, furan compounds, organic acids and monovalent inorganic salts. Representative examples of such fermentation inhibitors include aromatic compounds and furan compounds such as furfural, hydroxymethylfurfural, vanillin, vanillic acid, syringic acid, coniferyl aldehyde, coumaric acid and ferulic acid.

Examples of the organic acids and inorganic salts include acetic acid and formic acid; and salts of potassium, sodium and the like.

The sugar concentration in the concentrated sugar liquid may be arbitrarily within 50 g/L to 400 g/L depending on, for example, the use of the concentrated sugar liquid. When more complete removal of the fermentation inhibitors is desired, water may be added to the sugar liquid or the concentrated sugar liquid, followed by concentrating the resulting dilution through a nanofiltration membrane and/or a reverse osmosis membrane to a desired sugar concentration. By this, fermentation inhibitors can be removed as a permeate. Use of a nanofiltration membrane is more preferred than use of a reverse osmosis membrane, since a nanofiltration membrane has higher effect of removing fermentation inhibitors. Whether to use a nanofiltration membrane or to use a reverse osmosis membrane may be selected in consideration of the concentration of fermentation inhibitors contained in the mixed sugar liquid, or of how the fermentation at a later stage is influenced by the fermentation inhibitors.

The step of filtration through a microfiltration membrane to remove the insoluble substance(s), to obtain a sugar liquid as a permeate [Step (2)], is described below.

The precipitate containing magnesium hydroxide produced in the above step is filtered using a microfiltration membrane, to obtain a sugar liquid as a permeate.

Microfiltration membranes are also called membrane filtration, and are separation membranes that can separate and remove particles having sizes of about 0.01 to 10 μm from a particulate suspension using a pressure difference as a driving force. Microfiltration membranes have pores having sizes of 0.01 to 10 μm on their surfaces, and particulate components larger than the pores can be separated/removed to the membrane side.

Examples of the material of the microfiltration membrane include, but are not limited to, cellulose acetate, aromatic polyamide, polyvinyl alcohol, polysulfone, polyvinylidene fluoride, polyethylene, polyacrylonitrile, ceramics, polypropylene, polycarbonate and polytetrafluoroethylene (Teflon (registered trademark)). The membrane is preferably a polyvinylidene fluoride microfiltration membrane in view of contamination resistance, chemical resistance, strength, filtration performance and the like.

The average pore size of the microfiltration membrane is preferably 0.01 μm to 1 μm. This is because the size of the insoluble substance(s) in the concentrated cellulosic biomass sugar liquid to be precipitated by the alkaline precipitation is about 2 μm and, therefore, the precipitated insoluble substance(s) can be almost completely removed by filtration using a microfiltration membrane when the microfiltration membrane has an average pore size of 1 μm. On the other hand, when the average pore size of the microfiltration membrane is less than 0.01 μm, complete removal of the precipitated insoluble substance(s) is, of course, theoretically possible, but the filtration flow rate (flux) is low, and the filtration requires high pressure in such cases, which are problematic. Moreover, use of such a membrane often leads to occurrence of clogging (fouling) on the surface of the membrane, inside the membrane, or in minute voids on the module, due to the insoluble substance(s). Thus, it is preferred to use a membrane with an average pore size of not less than 0.01 μm, that is, a microfiltration membrane.

The microfiltration membrane treatment may be preceded by pretreatment by known solid-liquid separation, for example, centrifugation using a screw decanter or the like; filtration such as pressure or suction filtration; or membrane filtration such as microfiltration. The pretreatment can be effective means especially when the concentrated cellulosic sugar liquid contains a large amount of organic solids, lignin, undegraded cellulose, xylan, oligosaccharides and/or the like irrespective of the pH adjustment. It should be noted that, even when such solid-liquid separation is carried out, the insoluble substance(s) containing magnesium hydroxide cannot be removed without performing the filtration through a microfiltration membrane.

Examples of the mode of the filtration through an ultrafiltration membrane include cross-flow filtration and dead-end filtration. In view of prevention of fouling and securing of the flux, cross-flow filtration is preferred. Microfiltration membranes can be classified into flat membranes and hollow fiber membranes. A hollow fiber membrane is preferred. When a hollow fiber membrane is used, reverse washing can be carried out for removing dirt or scale components attached to the membrane surface, by applying pressure from the secondary side of the membrane using a solution containing an agent. Hollow fiber membranes can be classified into two types: internal pressure-type hollow fiber membranes (for filtration from the internal side to the external side) and external pressure-type hollow fiber membranes (for filtration from the external side to the internal side). In internal pressure-type hollow fiber membranes, insoluble substances containing magnesium are produced inside the hollow, and this may cause membrane clogging, which is not preferred. Thus, an external pressure-type hollow fiber membrane may be preferably used. Since, in particular, the component precipitated under alkaline conditions is magnesium hydroxide, the reverse washing is preferably carried out using an acidic agent. Examples of the acidic agent that may be preferably used include those having a pH of 0.4 to 4 containing sulfuric acid, hydrochloric acid or the like.

Method of Producing Chemical Product Using Sugar Liquid as Fermentation Feedstock By culturing microorganisms having capacities to produce various chemical products using, as a fermentation feedstock, the sugar liquid obtained by our method, the chemical products can be manufactured. "Culturing a microorganism using the sugar liquid as a fermentation feedstock" herein means that one or more of the sugar components and the amino sources contained in the sugar liquid are utilized as nutrients for a microorganism to allow growth of the microorganism and metabolic conversion of the sugars.

Specific examples of the chemical products include alcohols, organic acids, amino acids, nucleic acids and enzymes, which are substances mass-produced in the fermentation industry. Such chemical products are produced and accumulated inside and outside the living body in the process of metabolism using sugar components contained in the sugar liquid as carbon sources. Specific examples the chemical products that can be produced by the microorganisms include alcohols such as ethanol, 1,3-propanediol, 1,4-propanediol and glycerol; organic acids such as acetic acid, lactic acid, pyruvic acid, succinic acid, malic acid, itaconic acid and citric acid; nucleosides such as inosine and guanosine; nucleotides such as inosinic acid and guanylic acid; and amine compounds such as cadaverine. The sugar liquid can also be applied to production of enzymes, antibiotics, recombinant proteins and the like. The microorganisms to be used for production of such chemical products are not limited as long as the microorganisms are capable of efficiently producing the chemical products of interest. Examples of the microorganisms include *E. coli*, yeasts, filamentous fungi and Basidiomycetes.

As described above, the sugar liquid obtained by the method is a sugar liquid from which the magnesium component has been removed. Thus, the sugar liquid can be preferably used in a method of producing a chemical product by intermittent or continuous filtration using a separation membrane. The separation membrane to be used herein may be any of organic polymer membranes such as PVDF membranes; and inorganic separation membranes such as zeolite membranes. Since the sugar liquid processed is a sugar liquid from which the magnesium component has been removed, the sugar liquid has excellent long-term filterability, which is advantageous.

Apparatus that Produces Sugar Liquid

The apparatus that produces the sugar liquid is described below.

Figure 5:
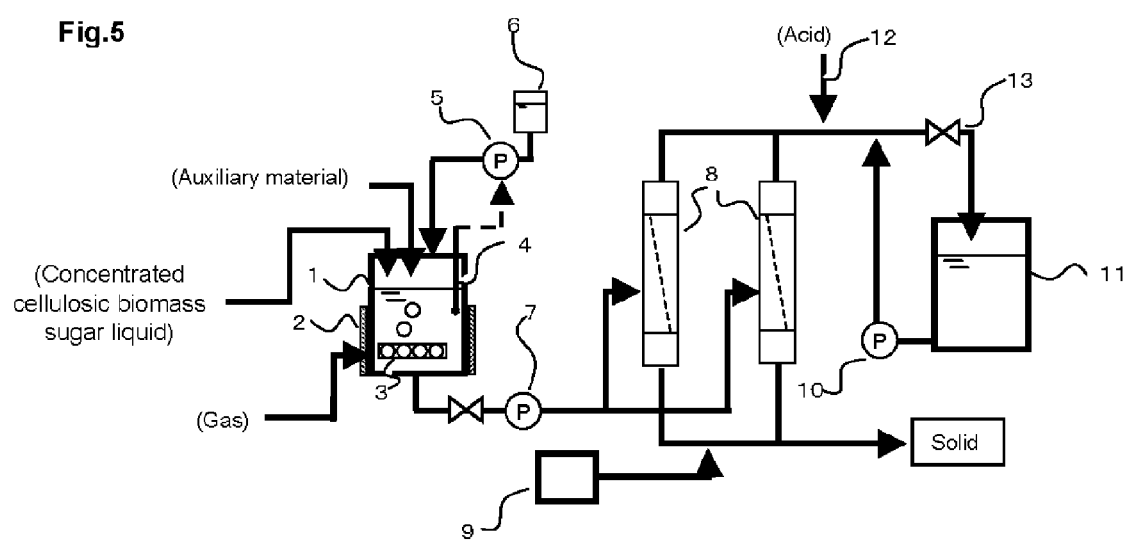
FIG. 5 is a side view illustrating an example of the apparatus used in our method of producing a sugar liquid.

FIG. 5 is a side view illustrating an example of the apparatus used in the method.

In FIG. 5, the concentrated cellulosic biomass sugar liquid is retained in a precipitation tank 1. The pH in the precipitation tank 1 is then adjusted. Examples of the method for the pH adjustment include a method in which an alkali is added from an alkali storage tank 6, and a method in which an alkali in the gas state such as ammonia gas is supplied from a diffuser tube 3. During addition of the alkali, the amount of the alkali to be added can be controlled by monitoring the pH in the precipitation tank 1 with a pH sensor 4 while sending a signal from the sensor to an alkali supply control pump 5. Also, when ammonia gas is used, the pH can be similarly adjusted while the amount of the gas is controlled with a valve. Air may be supplied from the diffuser tube 3 while the concentrated cellulosic biomass sugar liquid retained in the precipitation tank 1 is mixed to achieve a uniform pH and promote precipitation of magnesium hydroxide.

The precipitation tank 1 may be equipped with a thermostat 2. Either incubation or cooling may be carried out by the thermostat 2, and cooling is preferably carried out to make the precipitation of magnesium hydroxide more likely to occur. The temperature for the cooling is not limited as long as the concentrated cellulosic biomass sugar liquid is not frozen. The precipitation tank 1 connects to a microfiltration membrane module 8 through a microfiltration membrane pump 7. The microfiltration membrane mentioned above is arranged in the microfiltration membrane module 8. The microfiltration membrane module 8 may be provided with a compressed air supplier 9 placed inside the module to wash the membrane surface by aeration. By periodically using the compressed air supplier 9, dirt components attached to, or deposited on, the surface of the microfiltration membrane can be removed.

The filtrate component from the microfiltration membrane module 8 is collected into an MF filtrate tank 11. The solid component separated in the primary side of the microfiltration membrane module 8 is discharged as appropriate. When the microfiltration membrane module 8 is an external pressure-type hollow fiber membrane, reverse washing of the hollow fiber membrane can be carried out with the filtrate stored in the MF filtrate tank 11, by applying pressure from the filtrate side using a reverse washing pump 10. In such a case, the external pressure-type hollow fiber membrane can be washed with an aqueous acid solution supplied from an acid supply line 12, by supplying the acid from the acid supply line 12 into the pipe, closing a washing valve 13, and then applying pressure with the reverse washing pump 10. By the supply of the acid, magnesium hydroxide and the like precipitated on the membrane surface of the microfiltration membrane module 8 and in the channels can be removed by dissolution. By this, the filtration flux of the microfiltration membrane module 8 can be recovered. An auxiliary material may be supplied to the precipitation tank 1. When an auxiliary material is added to the concentrated cellulosic biomass sugar liquid, generation of an insoluble precipitate occurs in some cases. By preliminarily adding the auxiliary material to the precipitation tank 1, such a precipitate can be removed by the microfiltration membrane module 8. A gas may be supplied to the precipitation tank 1. In cases where ammonia gas, which is in the gas state, is fed as the alkali, the ammonia gas is especially preferably supplied from the diffuser tube 3.

Figure 6:
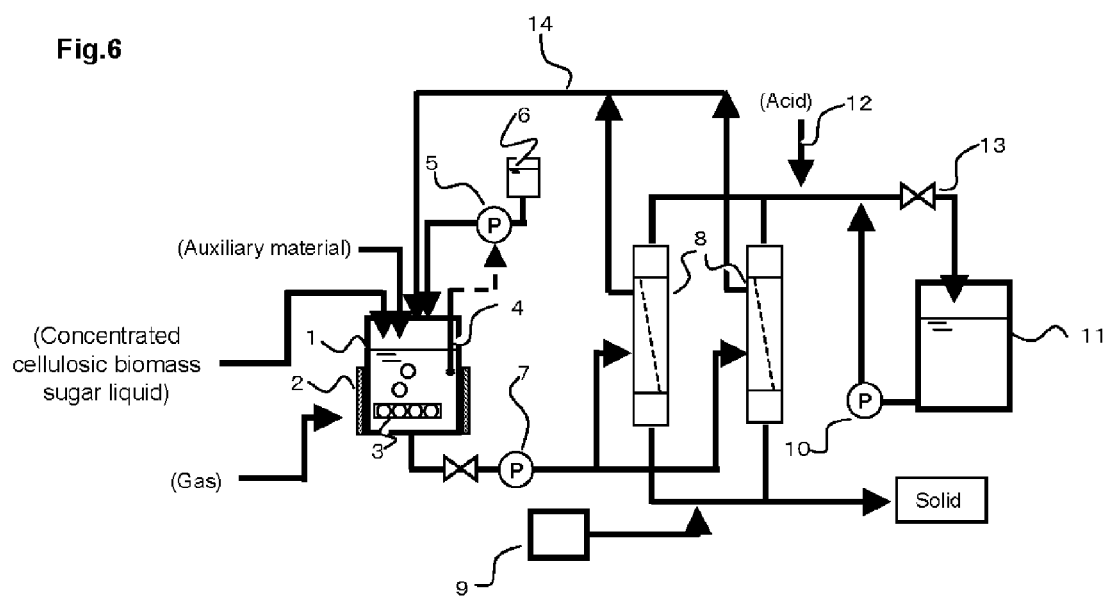
FIG. 6 is a side view illustrating another example of the apparatus used in the method of producing a sugar liquid.

FIG. 6 is a side view illustrating another example of the apparatus used in the method. This apparatus is the same as the apparatus shown in FIG. 5 except that a cross-flow return line 14 is included. In this apparatus, a liquid flow is generated on the membrane surface of the microfiltration membrane module 8 by a microfiltration membrane pump 7, to allow cross-flow filtration.

Fermentation Apparatus

An apparatus that produces a chemical product using the sugar liquid as a fermentation feedstock is described below.

Figure 7:
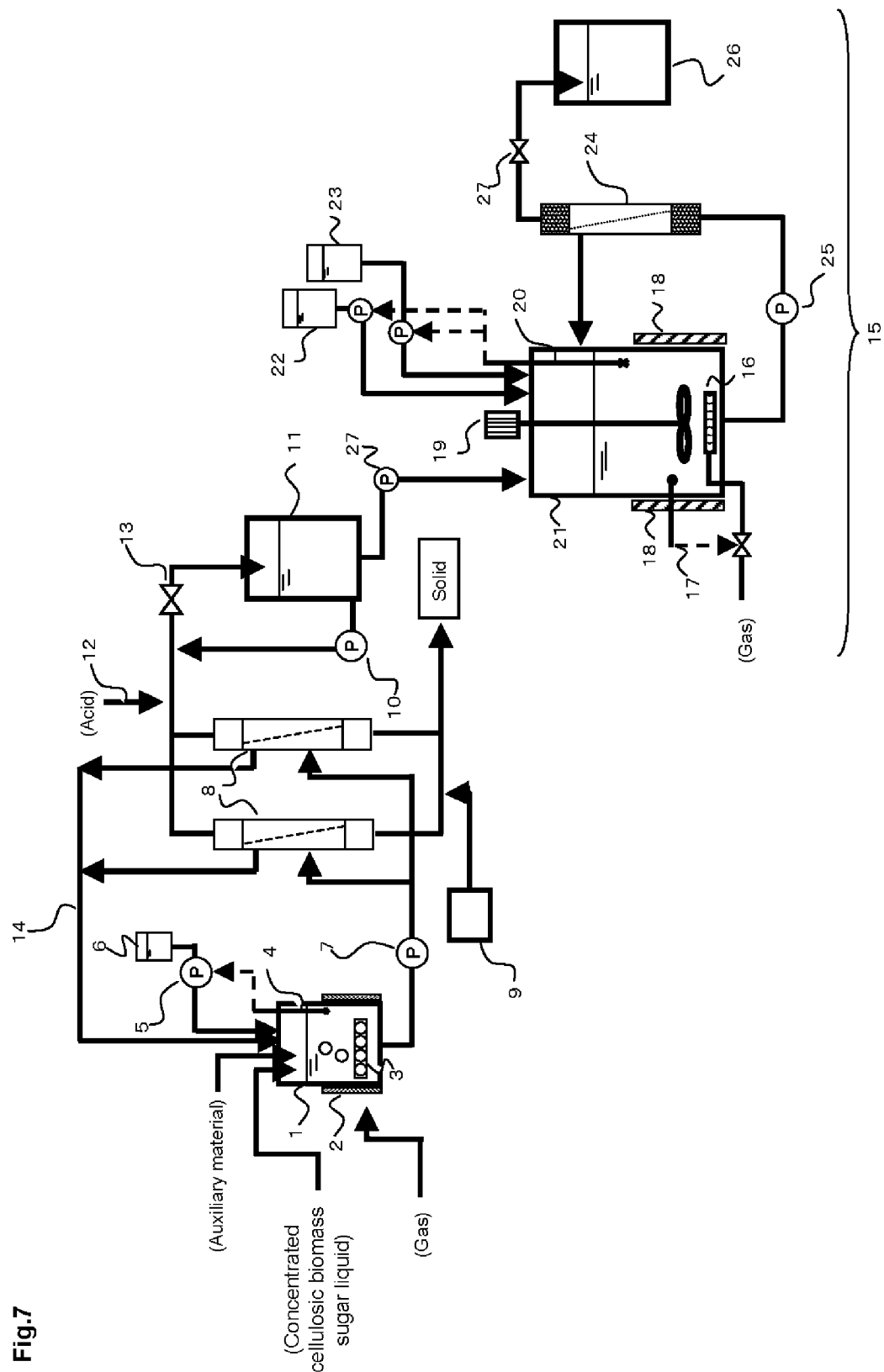
FIG. 7 is a side view illustrating an example of an apparatus that produces a chemical product using the sugar liquid as a fermentation feedstock.

FIG. 7 is a side view illustrating an example of an apparatus that produces a chemical product using the sugar liquid as a fermentation feedstock.

In FIG. 7, a fermentation apparatus 15 is provided with a fermenter 21 and a stirrer 19. In the fermenter 15, an incubator 18 is placed for adjustment of the temperature to an optimum temperature for culturing of the microorganism used. In particular, when the fermentation production of the chemical product is carried out under aerobic conditions, the amount of the gas fed to the fermenter 21 through a vent pipe 16 can be controlled by placing a DO sensor 17 in the fermenter 21 and measuring the dissolved oxygen level during the fermentation, while using a signal from the sensor for controlling a valve. The gas is selected from nitrogen, oxygen, air and the like. A pH sensor 20 may be provided, and signals from the sensor may be used to control supply of an acid from an acid supply tank 22 and feeding of an alkali from an alkali supply tank 23. The fermenter 21 may be provided with a microfiltration membrane module 24 for separation of microbial cells from a chemical product produced in the culture liquid. In the microfiltration membrane module 24, cross-flow filtration is preferably carried out using a cross-flow pump 25. The filtrate of the microfiltration membrane module 24 is collected in a culture filtrate storage tank 26. The sugar liquid flow rate is preferably controlled by a sugar liquid flow rate controller 27 such that the amount of the sugar liquid fed into the fermenter 21 is the same as the amount of the filtrate from the microfiltration membrane.

EXAMPLES

The method of producing a sugar liquid is described below concretely by way of Examples. However, this disclosure is not limited to these Examples.

Reference Example 1: Measurement of Sugar Concentration

The concentrations of glucose and xylose contained in the sugar liquid were measured under the HPLC conditions described below based on comparison with standard samples:

Column: Luna NH$_2$ (manufactured by Phenomenex, Inc.)
Mobile phase: MilliQ:acetonitrile=25:75 (flow rate, 0.6 mL/minute)
Reaction solution: None
Detection method: RI (differential refractive index)
Temperature: 30° C.

Reference Example 2: Production of Concentrated Cellulosic Biomass Sugar Liquid 1

Rice straw was used as a cellulose. The cellulose was immersed in water, and subjected to treatment using an autoclave (manufactured by Nitto Koatsu Co., Ltd.) with stirring at a temperature of 180° C. for 20 minutes. Thereafter, centrifugation (3000 G) was carried out to separate the solution component (hydrothermally treated liquid) from the solid (cellulose fraction). To each of the hydrothermally treated liquid and the cellulose fraction, "Accellerase DUET" (enzyme concentration, 40 g/L), manufactured by Genencor, was added (final concentration, 1 mg/L), followed by carrying out incubation at a temperature of 50° C. for 24 hours to perform hydrolysis. The obtained decomposition products of the hydrothermally treated liquid and the cellulose fraction were subjected to solid-liquid separation by centrifugation, and each supernatant was then filtered through a microfiltration membrane. The sugar concentration in each of the decomposition products of the hydrothermally treated liquid and the cellulose fraction was measured according to Reference Example 1. The results are summarized in Table 1 and Table 2.

Sugar enrichment through a nanofiltration membrane was carried out with the decomposition products of the cellulose fraction and the hydrothermally treated liquid, to obtain the concentrated sugar liquid 1 and the concentrated sugar liquid 2. As the nanofiltration membrane, a flat membrane "UTC-60," which is used in a nanofiltration membrane manufactured by Toray Industries, Inc. "SU-610," was cut out and used. The sugar concentration in each of the hydrolysates and the concentrated cellulosic biomass sugar liquids was measured according to Reference Example 1. The results are shown in Table 1 and Table 2. The turbidity (Nephelometric Turbidity Units; NTU) of each sugar liquid was quantified using a high-performance laboratory turbidimeter (2100N) manufactured by HACH. The pH of the concentrated sugar liquid 1 was 4.8, and the pH of the concentrated sugar liquid 2 was 3.8.

TABLE 1

|  | Glucose (g/L) | Xylose (g/L) | Turbidity (NTU) |
|---|---|---|---|
| Decomposition product of cellulose fraction | 58 | 14 | 0 |
| Concentrated sugar liquid 1 | 180 | 41 | 0 |

TABLE 2

|  | Glucose (g/L) | Xylose (g/L) | Turbidity (NTU) |
|---|---|---|---|
| Decomposition product of hydrothermally treated liquid | 2 | 12 | 0 |
| Concentrated sugar liquid 2 | 19 | 96 | 1 |

Reference Example 3: Production of Concentrated Cellulosic Biomass Sugar Liquid 2

Decomposition products of the cellulose fraction and the hydrothermally treated liquid prepared according to the procedure described in Reference Example 2 were concentrated under reduced pressure, to obtain the concentrated sugar liquid 3 and the concentrated sugar liquid 4. The concentration under reduced pressure was carried out using a rotary evaporator (manufactured by As One Corporation) at 80° C. by reducing the pressure to 200 hPa, to perform sugar enrichment. The sugar concentration and the turbidity of each of the obtained concentrated sugar liquids were measured according to Reference Example 2. The results are shown in Table 3.

TABLE 3

|  | Glucose (g/L) | Xylose (g/L) | Turbidity (NTU) |
|---|---|---|---|
| Concentrated sugar liquid 3 | 139 | 35 | 5 |
| Concentrated sugar liquid 4 | 8 | 76 | 14 |

The turbidities were higher than those observed in Reference Example 2, in which concentration through a membrane was carried out. This is assumed to be due to sugar denaturation by the heating.

Example 1: Adjustment of pH of Concentrated Cellulosic Biomass Sugar Liquid to not Less than 7 by Addition of Alkali The pH of each of the concentrated cellulosic biomass liquids 1 and 2 prepared in the Reference Example 1 was adjusted using sodium hydroxide (1 N) to 6, 7, 8, 9, 10, 11, 12 or 13. The sugar liquids after the adjustment to the predetermined pHs were left to stand for 1 hour at a temperature of 25° C. The turbidity (Nephelometric Turbidity Units; NTU) was then measured. The turbidity of each sugar liquid was quantified using a high-performance laboratory turbidimeter (2100N) manufactured by HACH. The results are shown in Table 4. The turbidity of each sugar liquid before the pH adjustment was 0 (zero) NTU.

TABLE 4

| pH | Untreated | 6 | 7 | 8 | 9 | 10 | 11 | 12 | 13 |
|---|---|---|---|---|---|---|---|---|---|
| Concentrated sugar liquid 1 | 0 | 3 | 10 | 14 | 27 | 32 | 52 | 52 | 56 |
| Concentrated sugar liquid 2 | 1 | 1 | 12 | 16 | 86 | 154 | 178 | 183 | 180 |
| Concentrated sugar liquid 3 | 5 | 7 | 20 | 28 | 35 | 49 | 65 | 68 | 64 |
| Concentrated sugar liquid 4 | 14 | 14 | 27 | 36 | 97 | 204 | 234 | 245 | 250 |

Remarkably increased turbidities were found in all of the concentrated sugar liquids (1 to 4) at the pHs of not less than 7, especially at the pHs of not less than 8. In particular, the turbidities of the concentrated sugar liquids 2 and 4, which were obtained from hydrothermally treated liquids, finally reached higher values compared to the turbidities of the concentrated sugar liquids 1 and 3. Based on comparison of the turbidities between the concentrated sugar liquids 1 and 2 and the concentrated sugar liquids 3 and 4, we found that the concentration by evaporation allows the turbidity of the sugar liquid to finally reach a higher value.

Example 2: Ion Chromatography Analysis of Insoluble Substance

The pH of the concentrated sugar liquid 1 obtained in the Example 1 was adjusted to 10, and the resulting sugar liquid was left to stand for 1 hour, followed by centrifuging (15,000 rpm, 5 minutes) 1 mL of the sample to separate and collect an insoluble substance as a precipitate. To the obtained precipitate, 1 mL of 1 N aqueous sulfuric acid solution was added to redissolve the insoluble substance. The resulting solution was then subjected to ion chromatography analysis (cation analysis) under the following conditions:

Analysis Conditions:
  Column: Ion Pac AS22 (manufactured by DIONEX)
  Mobile phase: 4.5 mM $Na_2CO_3$/1.4 mM $NaHCO_3$ (flow rate, 1.0 mL/minute)
  Reaction solution: None
  Detection method: Electric conductivity (by use of a suppressor)
  Temperature: 30° C.

Figure 3:
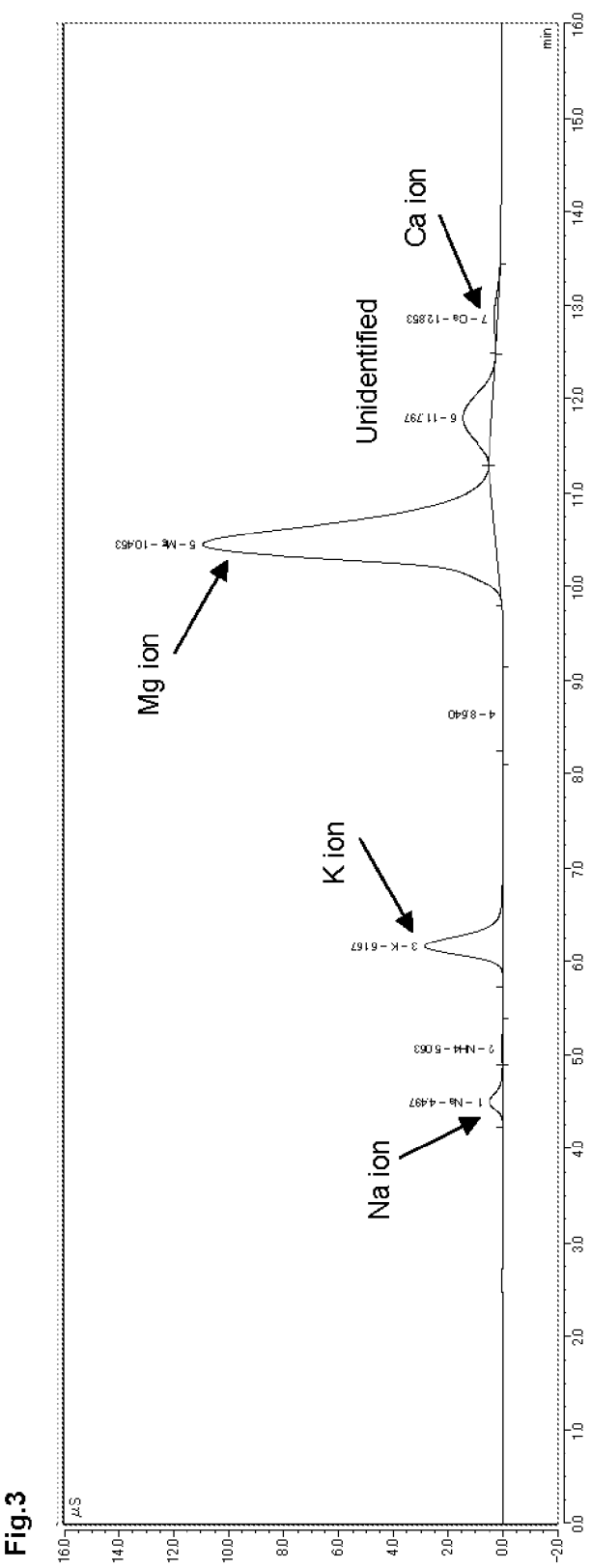
FIG. 3 is a chromatograph obtained by redissolving an insoluble substance in an aqueous hydrochloric acid solution and then performing separation by ion chromatography.

The chromatographic chart obtained by the above analysis is shown in FIG. 3. As a result of the analysis, peaks could be found at the positions corresponding to sodium ion (Na ion), potassium ion (K ion), magnesium ion (Mg ion) and calcium ion (Ca ion), and among these, Mg ion was found to be contained in an extremely large amount. Since alkalis and salts formed by Na ion or K ion are known to have high solubility even under alkaline conditions, these ions were assumed to be components dissolved in the sugar liquid, which also contained the insoluble substance. On the other hand, Mg ion is known to form magnesium hydroxide $(Mg(OH)_2)$ under alkaline conditions, and its solubility product $(K_{sp})$ is $1.2 \times 10^{12}$. Thus, this ion is insolubilized especially under alkaline conditions. That is, it was confirmed that the insoluble substance generated after the pH adjustment contained at least magnesium (magnesium hydroxide) as a component.

Example 3: Analysis of Particle Size of Insoluble Component Containing Magnesium Using 1 mL of the sample in Example 3 prepared by adjusting the pH of the concentrated sugar liquid 1 to 10 and leaving the resulting sugar liquid to stand for 1 hour, particle size measurement of the insoluble substance was carried out by the dynamic light scattering method (Otsuka Electronics Co. Ltd.). The cumulative number was set to 100. The results are shown in Table 5.

TABLE 5

| Particle size (nm) | f (ls) |
| --- | --- |
| 1446.31 | 0 |
| 1561.04 | 3.2 |

TABLE 5-continued

| Particle size (nm) | f (ls) |
| --- | --- |
| 1684.88 | 7.3 |
| 1818.53 | 11.5 |
| 1962.79 | 14.4 |
| 2118.5 | 15.1 |
| 2286.55 | 13.3 |
| 2467.94 | 9.8 |
| 2663.71 | 5.6 |
| 2875.02 | 2.1 |
| 3103.08 | 0 |
| 3349.24 | 0 |

The particle sizes of the insoluble substance were found to show a distribution centered around 2000 nm (2 μm).

Example 4: Microfiltration Membrane Treatment of Concentrated Cellulosic Biomass Sugar Liquid after pH Adjustment The pHs of the concentrated sugar liquid 1, concentrated sugar liquid 2, concentrated sugar liquid 3 and concentrated sugar liquid 4 prepared in Reference Example 2 and Reference Example 3 were adjusted to 10 using 28% aqueous ammonia (Wako Pure Chemical Industries, Ltd.), and the resulting sugar liquids were left to stand for 1 hour, to provide aqueous sugar solutions (concentrated sugar liquid 1A, concentrated sugar liquid 2A, concentrated sugar liquid 3A and concentrated sugar liquid 4A). Using each aqueous sugar solution as a test sample (1 L), filtration was performed using microfiltration membranes having different average pore sizes. The types and the average pore diameters of the membranes used are summarized in Table 6.

TABLE 6

| Product name | Average pore size (μm) | | Manufacturer |
| --- | --- | --- | --- |
| MF-40 | 0.4 | Yumicron Membrane Filter | Yuasa Co., Ltd. |
| MF-60 | 0.6 | (registered trademark) | Yuasa Co., Ltd. |
| MF-90 | 0.9 | | Yuasa Co., Ltd. |
| MF-250 | 2.5 | | Yuasa Co., Ltd. |
| HVLP | 0.4 | Durapore (registered trademark) | MILLIPORE |

Cross-flow filtration was performed by supplying each of the concentrated sugar liquids 1A to 4A at a pressure of 30 kPa at a temperature of 25° C., and an attempt was made to collect 0.5 L of a sugar solution from the membrane permeate side. The cross-flow filtration was carried out by setting each microfiltration membrane such that the membrane surface linear velocity was 30 cm/sec. and the membrane permeation flux was 0.1 m/day. As a result, all concentrated sugar liquids showed, only when MF-250 was used, decreases in filtration rates relative to those observed immediately after the filtration, and the filtration became impossible after collection of about 100 mL of the sugar solution. This was assumed to be due to entering of insoluble substance particles into pores of the microfiltration membrane to cause fouling since the average pore size of MF-250, 2.5 μm, was close to the average particle size, 2 μm, of the insoluble substance generated in the concentrated cellulosic biomass sugar liquid. On the other hand, with the microfiltration membranes with average particle sizes of 0.4 μm to 0.9 μm, no clogging of the membranes occurred, and filtration of 0.5 L of the sugar liquid could be completed. As a result of measurement of the turbidity of each filtrate, the turbidity was found to be 0 (zero) NTU for all membranes except MF-250.

Example 5: Fermentation Production of Ethanol Using Sugar Liquid as Fermentation Feedstock Filtrates obtained using the microfiltration membrane (HVLP) in Example 4 (the sugar liquid 1 and the sugar liquid 3) were used to carry out ethanol fermentation tests using an yeast (*Saccharomycecs cerevisiae* OC-2: wine yeast).

The above yeast was precultured using YPD medium (2% glucose, 1% yeast extract (Bacto Yeast Extract/BD) and 2% polypeptone (Nihon Pharmaceutical Co., Ltd.)) for 1 day at a temperature of 25° C. The pHs of the concentrated sugar liquid 1 and the concentrated sugar liquid 3 were adjusted to 6 using 1 N sulfuric acid, and the resulting sugar liquids were diluted to the sugar concentrations shown in Table 7 using sterile water before use. To these concentrated sugar liquids, the preculture liquid was added at 5%. After addition of the yeast, incubation was carried out at a temperature of 25° C. for 35 hours. The concentrations of ethanol accumulated in the culture liquids obtained by this operation were quantified by gas chromatography. The evaluation was carried out by detection and calculation with a hydrogen salt ionization detector using Shimadzu GC-2010 Capillary GC TC-1 (GL Science) 15 meter L.×0.53 mm I. D., df 1.5 µm. The obtained measurement results are shown in Table 7.

TABLE 7

|  | Glucose (g/L) | Xylose (g/L) | Ethanol (g/L) |
| --- | --- | --- | --- |
| Sugar liquid 1 | 45 | 10 | 18 |
| Sugar liquid 3 | 45 | 11 | 12 |

We found that ethanol can be produced with either the sugar liquid 1 or the sugar liquid 3. The sugar liquid 3 showed a lower ethanol productivity than the sugar liquid 1.

Comparative Example 1: Fermentation Production of Ethanol Using Sugar Liquid as Fermentation Feedstock 2

For comparison, sugar liquids before the filtration through the microfiltration membrane in Example 4 (the concentrated sugar liquid 1A and the concentrated sugar liquid 3A in Example 4, for which only the pH adjustment was carried out) were used to perform ethanol fermentation tests according to Example 5. The results are shown in Table 8. The concentrations of ethanol accumulated in the obtained culture liquids were found to be lower than those observed using the sugar liquids in Example 5, which were treated with the microfiltration membrane.

TABLE 8

|  | Glucose (g/L) | Xylose (g/L) | Ethanol (g/L) |
| --- | --- | --- | --- |
| Concentrated sugar liquid 1A | 45 | 10 | 13 |
| Concentrated sugar liquid 3A | 45 | 11 | 10 |

Example 6: Fermentation Production of Lactic Acid Using Sugar Liquid as Fermentation Feedstock Using the filtrates obtained in Example 4 using a microfiltration membrane (HVLP) (the concentrated sugar liquid 1 and the concentrated sugar liquid 3) and the *Lactococcus lactis* JCM7638 strain, fermentation production of lactic acid was studied.

For the above lactic acid bacterium, the pHs of the concentrated sugar liquid 1 and the concentrated sugar liquid 3 were adjusted to 6 using 1 N sulfuric acid, and the resulting sugar liquids were diluted with sterile water to the sugar concentrations shown in Table 9. To these sugar liquids, a preculture liquid containing the lactic acid bacterium was added at 5%. After addition of a yeast, incubation was carried out at a temperature of 25° C. for 35 hours. Static culture was performed for 24 hours at a temperature of 37° C. The concentration of L-lactic acid contained in the culture liquid was analyzed under the following conditions:

Column: Shim-Pack SPR-H (manufactured by Shimadzu Corporation)
Mobile phase: 5 mM p-toluenesulfonic acid (flow rate, 0.8 mL/min.)
Reaction solution: 5 mM p-toluenesulfonic acid, 20 mM Bis-Tris, 0.1 mM EDTA-2Na (flow rate, 0.8 mL/min.)
Detection method: Electric conductivity
Temperature: 45° C.

The results of L-lactic acid fermentation using the sugar liquid 1 and the sugar liquid 3 are shown in Table 9.

TABLE 9

|  | Glucose (g/L) | Xylose (g/L) | L-Lactic acid (g/L) |
| --- | --- | --- | --- |
| Sugar liquid 1 | 45 | 10 | 40 |
| Sugar liquid 3 | 45 | 11 | 30 |

We found that L-lactic acid can be produced with either the sugar liquid 1 or the sugar liquid 3. The sugar liquid 3 showed a lower lactic acid productivity than the sugar liquid 1.

Comparative Example 2: Fermentation Production of Lactic Acid Using Sugar Liquid as Fermentation Feedstock 2

For comparison, sugar liquids before the filtration through the microfiltration membrane in Example 4 (the concentrated sugar liquid 1A and the concentrated sugar liquid 3A, for which only the pH adjustment was carried out) were used to perform static culture of the *Lactococcus lactis* JCM7638 strain for 24 hours at a temperature of 37° C. The procedure was the same as in Example 6 except that the concentrated sugar liquids have not been subjected to microfiltration. The results of the fermentation using the concentrated sugar liquid 1A and the concentrated sugar liquid 3A are shown in Table 10. Lower L-lactic acid concentrations than in Example 6 were observed.

TABLE 10

|  | Glucose (g/L) | Xylose (g/L) | L-Lactic acid (g/L) |
| --- | --- | --- | --- |
| Concentrated sugar liquid 1A | 45 | 10 | 32 |
| Concentrated sugar liquid 3A | 45 | 11 | 28 |

Figure 4:
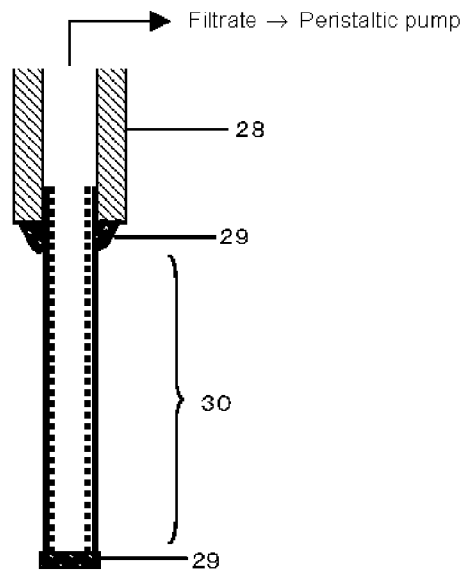
FIG. 4 is a schematic cross-sectional view for explanation of the constitution of a simplified module for the method of producing a sugar liquid which module uses a hollow fiber membrane.

Example 7: Filtration Through Hollow Fiber Microfiltration Membrane and Washing of Hollow Fiber Membrane The sugar liquid in Example 4 before the filtration through the microfiltration membrane (the concentrated sugar liquid 1AA) was used to perform filtration through a hollow fiber ultrafiltration membrane having an average pore size of 0.08 μm ("TORAYFIL" (registered trademark) HFS, manufactured by Toray Industries, Inc.). TORAYFIL HFS is a PVDF external pressure-type hollow fiber membrane, in which a solution is filtered from the external side to the internal side of the hollow fiber. TORAYFIL HFS was cut into a 10-cm piece, and one end of the membrane was sealed using a silicone adhesive. To the other end, a silicone tube (Laboran, 2×4) was attached using the above adhesive, to provide a simplified membrane module (FIG. 4). In FIG. 4, the silicone tube 28 is connected to the hollow fiber microfiltration membrane 30 with the silicone adhesive 29 such that a solution outside the hollow fiber microfiltration membrane can be filtered by reducing the pressure in the hollow fiber microfiltration membrane 30. One end of the hollow fiber microfiltration membrane 30 was sealed with the silicone adhesive 29.

The initial filtration flux was set to 1 m/day, and filtration was carried out for 24 hours. As a result, about 100 mL of a filtrate was obtained.

As a result of measurement of the membrane flux after 24 hours of the filtration, the membrane flux was found to have decreased to 0.2 m/day. To the silicone tube, 1 N aqueous sulfuric acid solution was connected, and reverse washing was carried out from the inside to the outside of the hollow fiber at a membrane flux of 0.1 m/day. The simplified membrane module was then washed well with RO water, and filtration of the concentrated sugar liquid was started again. As a result of measurement of the filtration flux at this time, the filtration flux could be confirmed to have recovered to 1 m/day.

Example 8: Filtration of Culture Liquid Through Hollow Fiber Microfiltration Membrane Using the simplified hollow fiber module prepared in the Example 7, the culture liquid 1 obtained after culturing the sugar liquid 1 of Example 6, and the culture liquid 1A obtained after culturing the sugar liquid 1A of Reference Example 2 were filtered, and the performance to separate the product, an aqueous lactic acid solution, from the microbial cells (lactic acid bacterium) was evaluated.

The separation was carried out by placing the simplified hollow fiber module of Example 7 in a beaker containing 100 mL of each culture liquid, placing a magnetic stirring bar in the beaker, and performing filtration with stirring at 100 rpm using a stirrer. The initial filtration flux was set to 0.5 m/day when the filtration was started. In the culture liquid 1A, the filtration became impossible 20 minutes after the start. In the culture liquid 1, the filtration could be continued for not less than 2 hours, and 8 mL of a filtrate (aqueous lactic acid solution) could be obtained. That is, it was shown that, in the production of the chemical product (lactic acid), use of the concentrated sugar liquid obtained by our method (concentrated sugar liquid 1) is more preferred for separation (membrane separation) of the fermentation product (aqueous lactic acid solution) from the culture liquid after the fermentation.

Example 9: Continuous L-Lactic Acid Fermentation

Using the continuous culture apparatus described in JP 2008-237213 A (FIG. 2) together with the filtrate obtained using the microfiltration membrane (HVLP) in Example 4 (sugar liquid 1) or the concentrated sugar liquid before the filtration through the microfiltration membrane in Example 5 (concentrated sugar liquid 1A), continuous fermentation with the lactic acid bacterium described in Example 7 was carried out. As a result, in the concentrated sugar liquid 1A, clogging of the membrane was found and the culture became impossible after 200 hours of the culture. On the other hand, in the sugar liquid 1, which was treated with the microfiltration membrane, continuous culture was possible for not less than 500 hours. That is, it could be confirmed a sugar liquid produced by our method can be preferably used as a sugar liquid to be used for continuous culture.

The invention claimed is:

1. A method of producing a fermentation feedstock comprising:
    obtaining a concentrated cellulosic biomass sugar liquid by enzyme treatment of a cellulosic biomass;
    adding an alkali(s) to the concentrated cellulosic biomass sugar liquid to adjust the pH to not less than 10 to precipitate an insoluble substance(s) containing at least magnesium hydroxide; and
    performing filtration through a microfiltration membrane to remove said insoluble substance(s) and obtain a fermentation feedstock as a permeate.

2. The method according to claim 1, wherein said concentrated cellulosic biomass sugar liquid is prepared by subjecting a hydrolysate obtained from the cellulosic biomass by enzyme treatment, to any one or more of treatments selected from the group consisting of membrane concentration, concentration under reduced pressure and concentration by heating.

3. The method according to claim 2, wherein average pore size of said microfiltration membrane is within the range of 0.01 μm to 1 μm.

4. The method according to claim 2, wherein said microfiltration membrane is a hollow fiber microfiltration membrane.

5. The method according to claim 2, wherein one or more additives selected from the group consisting of nitrogen sources, metal salts, vitamins, amino acids, sugars, antifoaming agents and surfactants are further added.

6. The method according to claim 1, wherein average pore size of said microfiltration membrane is within the range of 0.01 μm to 1 μm.

7. The method according to claim 6, wherein said microfiltration membrane is a hollow fiber microfiltration membrane.

8. The method according to claim 6, wherein one or more additives selected from the group consisting of nitrogen sources, metal salts, vitamins, amino acids, sugars, antifoaming agents and surfactants are further added.

9. The method according to claim 1, wherein one or more additives selected from the group consisting of nitrogen sources, metal salts, vitamins, amino acids, sugars, antifoaming agents and surfactants are further added.

10. The method according to claim 1, wherein said microfiltration membrane is a hollow fiber microfiltration membrane.

11. The method according to claim 10, wherein one or more additives selected from the group consisting of nitrogen sources, metal salts, vitamins, amino acids, sugars, antifoaming agents and surfactants are further added.

12. A method of producing a chemical product comprising culturing a microorganism using the fermentation feedstock obtained by the method according to claim 1.

13. A method of producing a chemical product comprising culturing a microorganism using the fermentation feedstock obtained by the method according to claim 1 to allow production of a chemical product in a culture liquid, while continuously or intermittently filtering said microorganism and said chemical product through a separation membrane to recover said chemical product.

* * * * *